(12) United States Patent
Muhlradt et al.

(10) Patent No.: US 7,316,996 B2
(45) Date of Patent: Jan. 8, 2008

(54) BISACYLOXYPROPYLCYSTEINE CONJUGATES AND THE USE THEREOF

(75) Inventors: Peter Muhlradt, Braunschweig (DE); Michael Morr, Wolfenbuttel (DE)

(73) Assignee: GBF Gesellschaft fur Biotechnologische Forschung mbH, Braunschweig (DE)

(*) Notice: Subject to any disclaimer, the term of this patent is extended or adjusted under 35 U.S.C. 154(b) by 0 days.

(21) Appl. No.: 10/521,013

(22) PCT Filed: Jul. 18, 2003

(86) PCT No.: PCT/EP03/07892

§ 371 (c)(1),
(2), (4) Date: Sep. 13, 2005

(87) PCT Pub. No.: WO2004/009125

PCT Pub. Date: Jan. 29, 2004

(65) Prior Publication Data

US 2006/0134061 A1      Jun. 22, 2006

(30) Foreign Application Priority Data

Jul. 19, 2002   (EP)   ................. 02016066

(51) Int. Cl.
*A61K 38/00*    (2006.01)
*A61K 38/02*    (2006.01)
*C07K 5/00*     (2006.01)
*C07K 5/06*     (2006.01)
*C07K 5/08*     (2006.01)
*C07K 7/00*     (2006.01)

(52) U.S. Cl. .................... 514/2; 514/18; 514/19; 514/186; 530/331; 530/359; 562/426; 562/556

(58) Field of Classification Search ............ None
See application file for complete search history.

(56) References Cited

U.S. PATENT DOCUMENTS 5,580,563 A * 12/1996 Tam ................. 424/197.11
6,573,242 B1 * 6/2003 Muehlradt ............. 514/14

FOREIGN PATENT DOCUMENTS

| EP | 0 510 356 | 10/1992 |
|----|-----------|---------|
| EP | 0 604 945 | 7/1994 |
| EP | 0 604 957 | 7/1994 |
| EP | 0 638 588 | 2/1995 |
| WO | WO 00/42175 | 7/2000 |

OTHER PUBLICATIONS

Muller MR, Pfannes SDC, Ayoub M, Hoffmann P, Bessler WG, Mittenbuhler K, Immunostimulation by the synthetic lipopeptide P3CSK4: TLR4-independent activation of the ERK1/2 signal transduction pathway in macrophages, Immunology, 2001, 103: 49-60.*
Esche UVD, Ayoub M, Pgannes SDC, Muller MR, Huber M, Wiesmuller KH, Loop T, Humar M, Fischbach KF, Strunkelnberg M, Hoffmann P, Bessler WG, Mittenbuhler K, Immunostimulation by bacterial components: I. Activation of macrophages and enhancement of genetic immunization by the lipopeptide P3CSK4, Int J of Immunopharm, 2000, 22: 1093-1102.*
Raghow R, THe role of extracellular matrix in postinflammatory wound healing and fibrosis, FASEB J, 1994, 8: 823-831.*
Annane D, Sebille V, Troche G, Raphael JC, Gajdos P, Bellissant E, A 3-level prognostic classification in septic shock based on cortisol levels and cortisol response to corticotropin, JAMA, 2000, 283(8): 1038-1045.*
Parrillo JE, Pathogenetic Mechanisms of Septic Shock, NEJM, 1993, 328(20): 1471-1478.*
Harris JM, Martin NE, Modi M, Pegylation, Drug Delivery Systems, Clin Pharmacokinet, 2001, 40(7): 539-551.*
Veronese FM, Peptide and protein PEGylation: a review of problems and solutions, Biomaterials, 2001, 22: 405-417.*
Roberts MJ, Bentley MD, Harris JM, Chemistry for peptide and protein PEGylation, Advanced Drug Delivery Reviews, 2002, 54: 459-476.*
Kim WJH, Cellular SIgnaling in Tissue Regeneration, Yonsei Medical Journal, 2000, 41(6): 692-703.*
Sepsis and Septic Shock from the Merck Index.*
XP-002257581 Rharbaou i et al. "The Mycoplasma-derived lipopeptide MALP-2 is a potent mucosal adjuvant" Eur. J. Immunol, 2002, 32; 2857-2865.
XP-002237893, Polyethylene Glycol; pp. 392-393 & 398.
XP-002257580 Takeuchi et al."Cutting Edge: Preferentially the R-Stereoisomer of the Mycoplasmal Lipopetide Macrophage-Activating Lipopeptide -2 Activates Immune Cell Through a Toll-Like Receptor 2-and MyD88-Dependent Signaling Pathway" Cutting Edge; pp 1-4, 2000.
Metzger et al. "Synthesis of N-Fmoc protected derivatives of S-(2,3 dihydroxypropyl)-cysteine and their application in peptide synthesis" Int. J. Peptide Protein Res. 38 1991; pp. 545-554.
Hoffmann et al. "Stimulation of Human and Murine Adherent Cells by Bacterial Lipoprotein and Synthetic Lipopeptide Analogues" Immunbiol., vol. 177, pp. 158-170 1988.
Metzger et al. "Synthesis of novel immunologically active tripalmitoyl-S-glycerlcysteinyl lipopeptides as useful intermediates for immunogen preparations" Int. J. Peptide Protein Res. 37, 1991, pp. 46-57.
Muhlradt et al. "Purification and Partial Biochemical Characterization of a Mycoplasma fermentans-Derived Substance That Activates Macrophages To Release Nitric Oxide, Tumor Necrosis Factor, and Interleukin-6" Infection and Immunity, Sep. 1994 pp. 3801-3887, vol. 62 No. 9.

* cited by examiner

*Primary Examiner*—Anish Gupta
*Assistant Examiner*—Julie Ha
(74) *Attorney, Agent, or Firm*—Whitham, Curtis, Christofferson & Cook, PC

(57) ABSTRACT

The invention provides lipopeptide conjugates in which a cysteine that is double-substituted by a fatty acid is bonded by means of the carboxyl group to a highly soluble, physiologically compatible and non-immunogenic, polymeric conjugate group. The conjugates exhibit an excellent macrophage stimulant action and do not require addition solutizing. They can be used in a wide range of applications, in particular for stimulating macrophages, for stimulating antibody synthesis, for combating infection, as an immunostimulant, in particular in relation to tumors, for preventing and treating septicaemic shock, for would healing and as an adjuvant for vaccines.

15 Claims, 6 Drawing Sheets

BISACYLOXYPROPYLCYSTEINE CONJUGATES AND THE USE THEREOF

BACKGROUND OF THE INVENTION

1. Field of the Invention

The invention relates to novel bisacyloxypropylcysteine conjugates and their use, including in the form of pharmaceutical compositions.

2. Description of Related Art

It has been known for a long time that certain lipopeptides are macrophage activators (Hoffman, P., S. Heinle, U. F. Schade, H. Loppnow, A. J. Ulmer, H. D. Flad, G. Jung, and W. Bessler, 1988, "Stimulation of human and murine adherent cells by bacterial lipoprotein and synthetic bisacyoxypropylcysteine analogues", Immunobiol. 177:158-170). Peptides or proteins which are multiply fatty acid-substituted (acyloxy-substituted) at a propylcysteine residue, and which have a physiological effect, are also known, in particular, within this class of macrophage activators.

However, peptides, and among these lipopeptides having relatively long fatty acid chains, in particular, frequently suffer from what is a serious disadvantage for pharmaceutical and related uses in the human or animal body, i.e that of having too low a solubility in water, with this greatly restricting their activity and their area of use.

These problems can be solved by conjugating the proteins or peptides to water-soluble polymers. For example, EP 0 510 356 B1 discloses polyethylene glycol-protein conjugates in which a protein is bonded to a polyethylene glycol by way of a linker and thereby made considerably more water-soluble. EP 0 510 356 B1 mentions a large number of other documents which describe conjugating peptides or proteins to water-soluble polymers, in this case polyethylene glycol in particular. The conjugation with PEG is nowadays also termed "pegylating".

Macrophage activators which are pegylated in the above-described manner are already known. For example, a PEG which is acyloxy-substituted three times at a propyl-cysteine residue, i.e. tripalmitoyl-S-glycerylcysteine-polyethylene glycol, which can be designated $PAM_3$-Cys-PEG, can be obtained commercially.

$PAM_3$-Cys-PEG possesses the structure

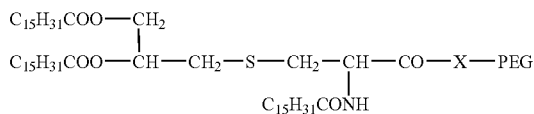

with the fatty acid-substituted propylcysteine being conjugated to the polyethylene glycol at position X by way of a divalent radical such as —NH—, —OCO—, —S—, —O— or the like.

Despite the very greatly improved water solubility of $PAM_3$-Cys-PEG as compared with the corresponding $PAM_3$-Cys peptides, it is frequently necessary, or at least very advisable, to add an organic solubilizer when using this substance as a macrophage activator since the macrophage activation would otherwise be lower. However, solubilizers such as octylglucoside are not entirely without problems from the pharmacological point of view.

There still remains, therefore, a great need for novel, physiologically well-tolerated, in particular non-immunogenic, macrophage activators which exhibit good solubility in water and are active. The object of the invention is therefore to make available such a novel well-tolerated, water-soluble and highly active macrophage activator.

BRIEF SUMMARY OF THE INVENTION

This object is achieved by means of a bisacyloxypropylcysteine conjugate according to formula (1),

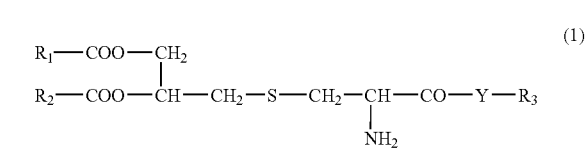

where $R_1$ and $R_2$ can be identical or different and are fatty acid radicals which are bonded by way of the carboxyl group, Y=—NH—, —O—, —S— or —OCO—, $R_3$ is a covalently, ionically or associatively bonded conjugate radical, in particular a water-soluble and physiologically tolerated, covalently or ionically bonded polymer, in particular covalently bonded polyethylene glycol (polyoxyethylene), —$(CH_2$—$CH_2$—$O)_m$—$CH_2$—$CH_2$—X, where X=OR, $NR_2$, SR or COOR, and R=H, benzyl- or $C_{1-6}$-alkyl, where several radicals R can be identical or different, a polyoxyethylene-polyoxypropylene copolymer, a dextran, a sugar, a polyvinylpyrrolidone, an alginate, a pectin or a collagen, and where the polymeric radical $R_3$ is substituted once, twice or several times by

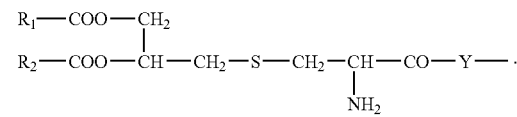

DETAILED DESCRIPTION OF THE INVENTION

Figure 1:
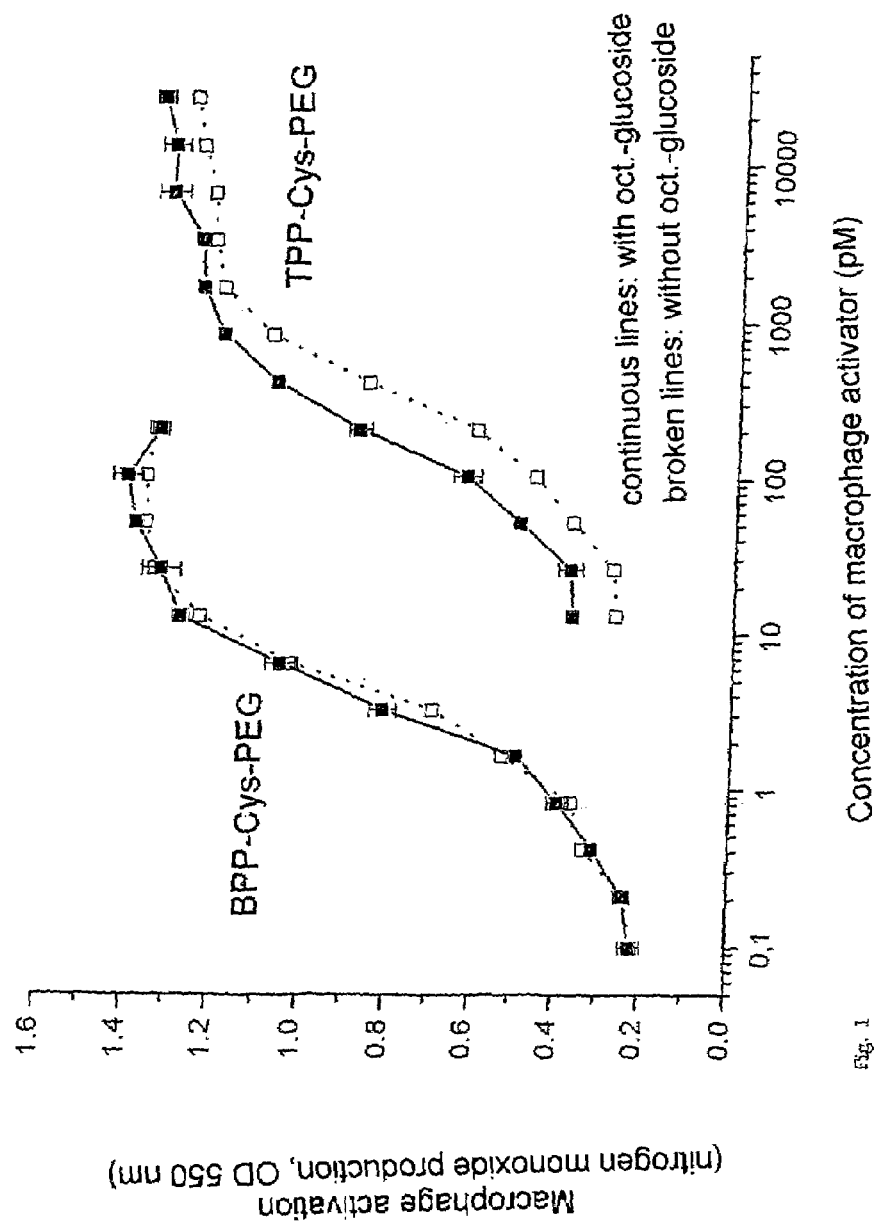
FIG. 1: The concentration dependence of macrophage activation, as measured by means of nitrogen monoxide production (determined spectroscopically at OD 550 nm), on the concentration of macrophage activator, in picomol.

The conjugate according to the invention can be present either as a racemate or as optically pure substances.

The bisacyloxypropylcysteine conjugate according to the invention is preferably a S-[2,3-bis(acyloxy)-(2S)-propyl]-L-cysteinylcarboxypolyethylene glycol (BAP-Cys-PEG) in which the polyethylene glycol is bonded on by way of the carboxyl group of the cysteine and the amino group of the cysteine remains free. In another embodiment, the bisacyloxypropylcysteine conjugate according to the invention is preferably a S-[2,3-bis(acyloxy)-(2R)-propyl]-L-cysteinylcarboxy-polyethylene glycol (BAP-Cys-PEG) in which the polyethylene glycol is bonded on by way of the carboxyl group of the cysteine and the amino group of the cysteine remains free. Customary modifications and substitutions, which are known to the chemist, can be performed on the molecule while retaining its function or, in this case, its physiological effect.

The radicals $R_{1,2}$ of the bisacyloxypropylcysteine conjugate according to the invention can be identical or different. Those which are preferred at present are $C_{7-25}$-, preferably $C_{8-22}$-alkyl, -alkenyl or -alkynyl groups, with the unsaturated positions preferably being present in the cis configuration. The alkyl, alkenyl and alkynyl radicals can be branched or unbranched, cyclic or cycloalkyl-substituted radicals. Suitable radicals $R_1$ and $R_2$ are sufficiently well known from fatty acid chemistry.

With regard to the group Y, it is simply a matter of establishing a stable linkage to the conjugate radical $R_3$ so as to ensure that the bisacyloxypropylcysteine is adequately bonded to $R_3$ and thereby remains water-soluble.

The radical $R_3$ is preferably a polyethylene glycol radical. However, in a general manner, this radical is a covalently, ionically or associatively bonded, physiologically tolerated conjugate radical which is suitable for converting the bisacyloxypropylcysteine into an active water-soluble form. Covalently bonded polymers are presently preferred. However, as an alternative, the conjugate radical can also be a dextran, a sugar, a polyvinylpyrrolidone, an alginate, a pectin or a collagen. In particular, dextran is used as a blood expander and is unobjectionable in view of the fact that it is physiologically tolerated.

Particularly in the case of highly polymerized conjugate radicals, it is also possible for several BAP-Cys units to be bonded to one conjugate radical $R_3$.

The molecular weight of the water-soluble polymer radical is preferably selected such that it amounts to from 100 to 30 000 daltons per bisacyloxypropylcysteine molecule. In the case of polyethylene glycol, a chain length m of from 5 to 700, preferably of from 100 to 500, is preferred but not imperative.

In one preferred embodiment, the S-[2,3-bis(acyloxy)-(2S)-propyl]-L-cysteinylcarboxypolyethylene glycol is a S-[2,3-bis(palmitoyloxy)-(2S)-propyl]-L-cysteinyl-carboxypolyethylene glycol. In another preferred embodiment, the S-[2,3-bis(acyloxy)-(2R)-propyl]-L-cysteinylcarboxypolyethylene glycol is a S-[2,3-bis(palmitoyloxy)-(2R)-propyl]-L-cysteinylcarboxy-polyethylene glycol.

The bisacyloxypropylcysteine conjugate according to this invention exhibits the advantage, as compared with previously known macrophage activators, that it combines good solubility in water with a macrophage activity which is comparatively very high (see below). It is not immunogenic, which means that no antibodies develop against the preparation when it is used in humans or animals.

The invention furthermore encompasses pharmaceutical compositions which comprise the bisacyloxypropyl-cysteine conjugates according to the invention. These compositions include, inter alia, solutions of the bisacyloxypropylcysteine conjugate according to the invention. Additional pharmaceutical additives and auxiliary substances can be present in these compositions. In particular, the bisacyloxypropyl-cysteine conjugate can be bonded, or adsorbed, to a pharmaceutically acceptable excipient. Suitable excipients are known to the skilled person and are also available commercially.

The pharmaceutical composition is preferably present in the form of a formulation which is suitable for injection, for inhalation or for intranasal or topical administration, with excipient-bonded administration forms being included. Ointments, creams, tinctures, solutions and the like, inter alia, are provided for local administration, as known to the skilled person for this purpose.

The bisacyloxypropylcysteine conjugates according to the invention, or the appurtenant pharmaceutical compositions, can be employed, inter alia, for stimulating macrophages, for stimulating antibody synthesis, for defense against infection, for stimulating immunity, particularly in regard to tumors, for preventing and treating septic shock, for wound healing and as an adjuvant for vaccines.

Substances which are administered together with the actual antigen (i.e. the substance which provokes the desired immune reaction) in connection with an immunization in order to augment the humoral and/or cell-mediated immune response are termed adjuvants.

The use of optimal adjuvants is of crucial importance when employing substances for immunization. Antigens only rarely mediate an adequate immune response when they are administered without adjuvants. In addition to this, it is not only a matter of the strength of the elicited immune response but also a matter of its quality. Stimulating an incorrect immunization pattern can lead to immunopathologic reactions and a deterioration of the symptoms of the infection. In this connection, the adjuvant can help to support the desired immune reaction.

Adjuvants can be combined, to form vaccines, with a very wide variety of antigens. The antigens which are selected can, in particular, be target antigens for the prophylactic treatment of infectious diseases, tumors, autoimmune diseases, allergies and chronic or acute inflammatory diseases. A vaccination is also understood as being a treatment with antigens for monitoring fertility in human or animal populations.

These uses encompass activating macrophages/monocytes or other cells which carry the receptor combination toll-like receptors 2 and 6, with all the indirect consequences due to mediators, in animals or humans. This implies the use, as adjuvant (that is as an adjunct for vaccines), for tumor therapy in the widest sense, including the in-vitro priming against tumor antigens of autologous cells which are to be reimplanted, or by means of direct therapy, which can be effected locally or systemically, for generating crosstolerance against endotoxin or other corresponding microbial components, which protects against sepsis, and for accelerating wound healing.

EXAMPLES

1. Synthesizing a bisacyloxypropylcysteine according to the invention where $R_1$ and $R_2$=palmitoyl, Y=NH and $R_3$=PEG A. (I) is synthesized in accordance with a described method (Metzger, J., Wiesmüller, K.-H., Schaud, R., Bessler, W. G., and Jung, G., 1991, "Synthesis and novel immunologically active tripalmitoyl-S-glycerylcysteinyl bisacyloxypropylcysteines as useful intermediates for immunogen preparations". Int. J. Pept. Protein Res. 37:46-57; Metzger, J. W., Wiesmüller, K.-H., and Jung, G., 1991, "Synthesis of N-Fmoc protected derivatives of S-(2,3-dihydroxypropyl)-cysteine and their application in peptide synthesis", Int. J. Pept. Protein Res. 38:545-554).

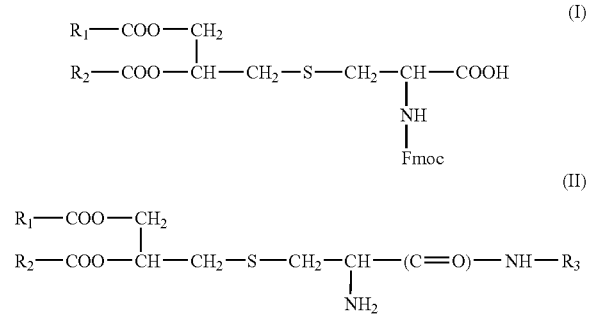

in particular where: $R_{1,2}=C_{15}H_{31}$—(palmitoyl-) and $R_3=$—$(CH_2—CH_2—O)_x—CH_2—CH_2—NH_2$ B. The carboxyl group is subsequently linked, using known methods (carbodiimide synthesis), to, for example, polymers which contain water-soluble $NH_2$ groups, e.g. diamino-PEG.

Example 34 mg (38 µmol) of (I) are dissolved in 1 ml of dry dimethylformamide/dichloromethane 2:1 after which 6 µl (38 µmol) of diisopropylcarbodiimide and 6 mg (38 µmol) of 1-hydroxybenzotriazole are added consecutively. 76 mg (38 µmol) of diamino-PEG 2000 are added to this mixture. After 24 hours at room temperature, the mixture is concentrated down to dryness and the Fmoc protective group is eliminated using 20% piperidine in dimethylformamide. The compound (II) is purified by means of silica gel chromatography. It is characterized by means of NMR and mass spectroscopy. It is further purified by means of HPLC on a C18 column at 40° C., buffer 1: 0.1% TFA in water; buffer 2: 0.1% TFA in 2-propanol. The substance elutes at approx. 80% V/V of buffer 2.

Content analysis is effected by means of fatty acid determination using internally admixed C14 standard, after hydrolysis and GLC, in accordance with standard methods, or by means of amino group determination using fluorescamine.

C. Biological Testing:

In principle, the activation of macrophages and monocytes can be measured by a large number of parameters, for example by means of the release of cytokines, chemokines or arachidonic acid metabolites in cultures of human monocytes or murine peritoneal macrophages. The test which is used here is based on the simultaneous stimulation of mouse peritoneal macrophages with interferon-γ and macrophage activator, e.g. BAP-Cys-PEG, so as to release nitrogen monoxide. (Reference: Muhlradt, P. F., and Frisch, M., 1994, "Purification and partial biochemical characterization of a Mycoplasma fermentans-derived substance that activates macrophages to release nitric oxide, tumor necrosis factor, and interleukin-6", Infect. Immun. 62:3801-3807).

Nitrogen Monoxide Release Assay:

In brief, peritoneal macrophages from C3H/HeJ mice were used as the macrophage source. They were cultured in 96-well microtiter plates and stimulated simultaneously with rIFN-γ and a serial dilution of macrophage activator. Insofar as necessary, the macrophage activators were dissolved in 25 mM octylglucoside in the first dilution step and then diluted further with medium. After an incubating time of 45-48 hours, the nitrate was reduced with nitrate reductase and the starting substance nitrogen monoxide was determined, as the sum of nitrate and nitrite, using Griess' reagent.

1 unit (U)/ml is defined as the dilution at which half-maximal stimulation takes place.

The results of the macrophage activation test are shown in FIG. 1.

It can be seen from the figure that bispalmitoyloxypropylcysteine-PEG (BPP-Cys-PEG), i.e. a macrophage activator according to this invention, has a markedly higher potential for activating macrophages than has the known $PAM_3$-Cys-PEG (in this present case designated TPP-Cys-PEG). The figure shows that BPP-Cys-PEG already achieves the same degree of macrophage activation at a concentration which is approx. forty times lower than that of TPP-Cys-PEG.

The figure furthermore shows that this outstanding and unexpected activation effect in the case of BPP-Cys-PEG is not noticeably improved by adding a solubilizer, in this case octylglucoside, whereas such an addition is required for the effect of $PAM_3$-Cys-PEG to be displayed optimally.

The novel bisacyloxypropylcysteine conjugate according to this invention does not, therefore, require any additional, and possibly physiologically disadvantageous, solubilization by means of an organic solvent or detergent.

Another advantage of BAP-Cys-PEG as compared with PAM3-Cys-PEG is the greater cell specificity, which can be attributed to the fact that this substance requires the cooperation of toll-like receptors 2 and 6 whereas the simultaneous presence of toll-like receptors 1 and 2 on the cell to be stimulated is sufficient for stimulation by $PAM_3$-Cys-PEG. The expression of toll-like receptor 6 is restricted to specific cells whereas toll-like receptor 1 is expressed ubiquitously by almost all the cells in the body.

2. Wound healing in diabetic mice

As in the case of diabetic patients, wound healing is also disturbed in diabetic mice and proceeds more slowly than in wild-type mice. The diabetic mouse is therefore an established animal model for wound healing.

An area of approx. 4×4 cm in size was shaved on the backs of 20 diabetic mice (32 C57BKLS/Bom-db) and this area was depilated with Veet two days later, after which the cream was carefully removed. After a further two days, the depilated backs of the mice were disinfected with Braunol.

After anaesthesia had been initiated with isoflurane/air, an additional local anaesthesia was performed by means of the i.c. injection of 2% xylocaine directly into the site envisaged for the excision, and the skin was defatted with trichloroethylene. After that, scissors were used to cut out a circular skin wound of 1.3 cm in diameter in each of the mice. The wounds were closed with a transparent plaster (Hydrofilm, F. Hartmann) and dressing adhesive. An additional, larger plaster, having an aperture corresponding to the wound, making possible continued observation of the wound, was adhered on top of the first plaster.

3×200 kUnits of BPP-Cys-PEG, in methylcellulose and 5% mouse serum (as carrier), were administered, per animal, through the transparent plaster on days 0, 2 and 5.

Control mice were only given the carrier mixture. The mice were observed for a period of 29-30 days. The plasters were changed at what were normally intervals of 5 days.

Figure 2:
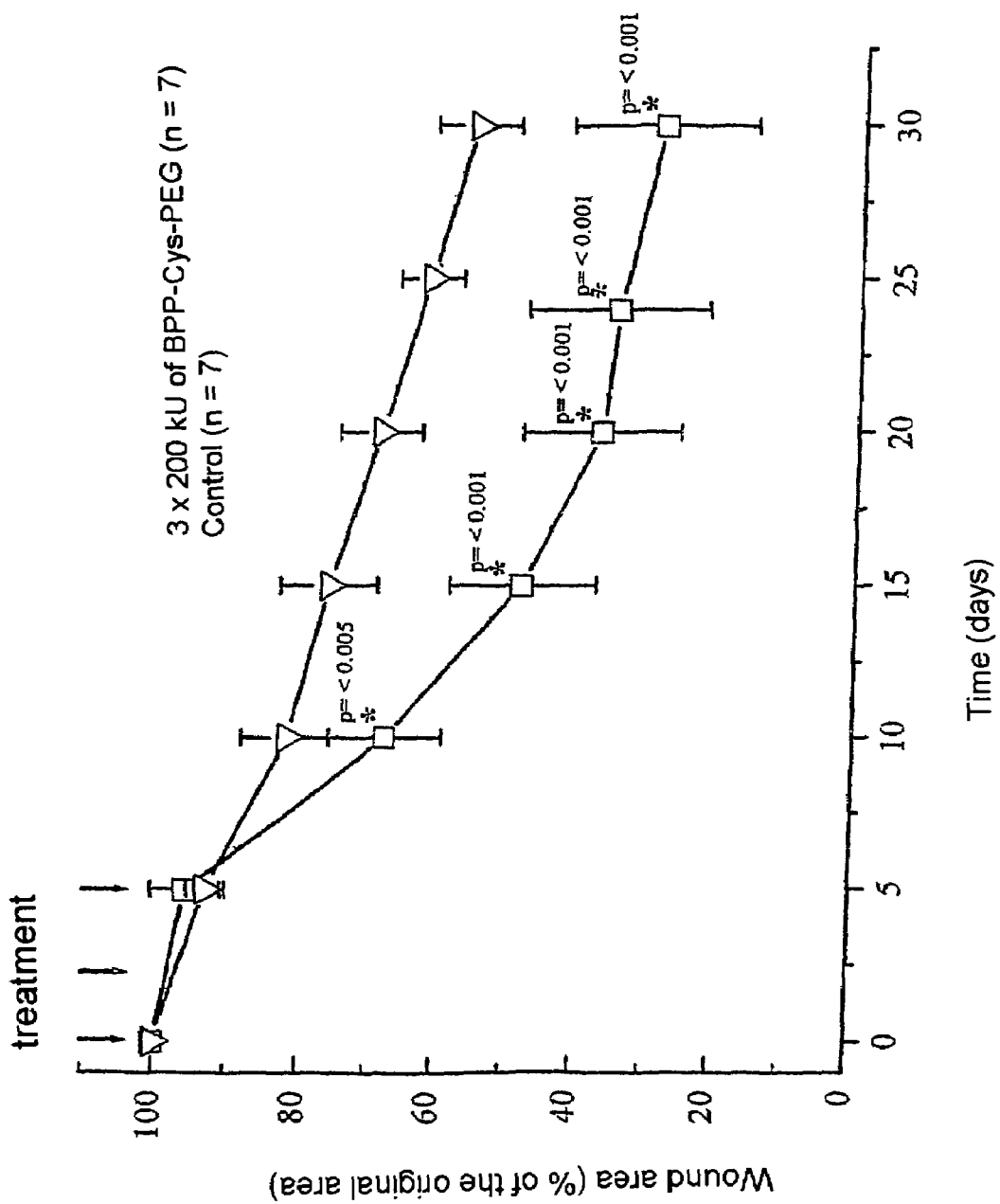
FIG. 2: Acceleration of wound healing in diabetic mice due to the triple administration of BPP-Cys-PEG. Triangular symbols: carrier-treated control animals; square symbols: BPP-Cys-PEG-treated animals.

Administering BPP-Cys-PEG (3×200 kU) accelerated the wound healing significantly (see FIG. 2).

3. Using MALP-2 derivatives or BPP-Cys-PEG as a mucosal adjuvant for eliciting an effective humoral response at both the systemic and mucosal levels. Experimental procedure:

6-8-week-old female BALB/c (H-2d) mice (Harlan Winkelmann GmbH, Borchen, Germany) were used for the experiments. Groups of in each case 5 mice were administered 50 µg of β-galactosidase (β-gal) (Boehringer, Mannheim, Germany), either on its own or together with 0.5 µg of synthetic R-MALP-2, S-MALP-2 or BPP-Cys-PEG, as adjuvant, by the nasal route (25 µl) on days 1, 14 and 21. Serum samples were withdrawn on day 31 and stored at −20° C. until the β-gal-specific antibodies were determined. Nunc-Immuno MaxiSorp test plates containing 96 wells (Nunc, Roskilde, Denmark) were coated with 100 µl of β-gal (Boehringer, Mannheim, Germany), containing 5 µg/ml in 0.05 mol carbonate buffer (pH 8.2), per well. Serial double dilutions of the sera or washings in PBS containing 1% BSA and 0.05% Tween 20 were added (100 µl/well) and the plates were incubated at 37° C. for 2 hours. After the plates had been washed, biotinylated γ-chain-specific goat anti-mouse IgG (Sigma Chemie, Deisenhofen, Germany) was added and the plates were incubated at 37° C. for a further hour. After the plates had been washed four times, 100 µl of peroxidase-conjugated streptavidin (Pharmingen) were added to the wells and the plates were incubated at 37° C. for 30 minutes. After the plates had been washed four times, the reactions were developed with ABTS in 0.1 mol citrate phosphate buffer (pH 4.35) containing 0.01% $H_2O_2$. The titers at the end point were given as the reciprocal $log_2$ of the last dilution which, after a 30-minute incubation, gave an optimal density at 405 nm of 0.1 units above the values of the negative controls after a 30 minute incubation.

Figure 3:
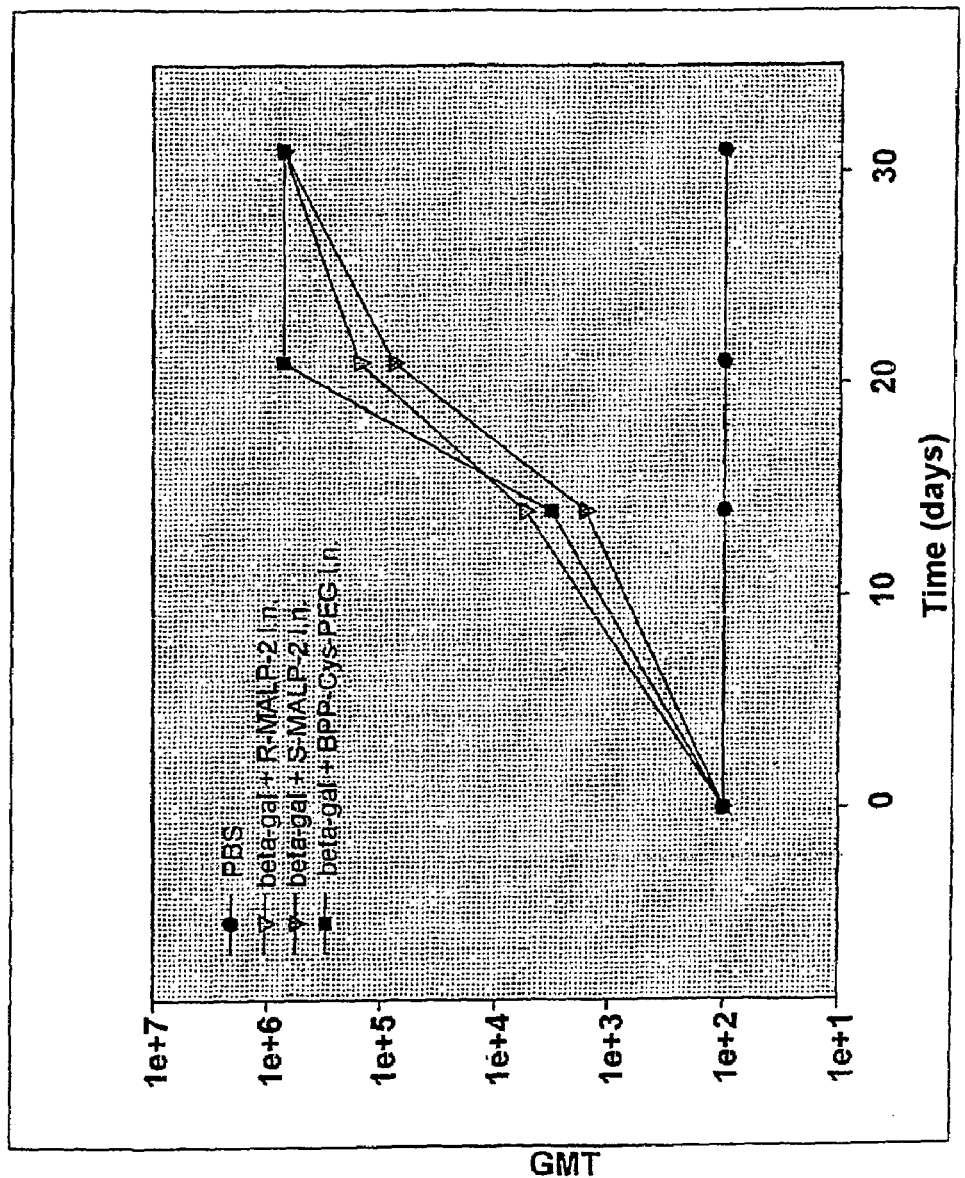
FIG. 3: Humoral responses which are stimulated after inoculating with MALP-2 derivatives and BPP-Cys-PEG, as mucosal adjuvants, at a dose of 0.05 μg per animal per immunization. The mice were immunized intranasally, on days 0, 7 and 14, with β-galactosidase (50 μg/dose) mixed with the above derivatives. On day 31 after the first immunization, serum samples were withdrawn and the concentrations of the β-galactosidase-specific antibodies were determined by means of ELISA. The results are depicted as end point titers.

Vaginal and lung washings were obtained by rinsing the organs with 1 mm PBS which contained 50 mM EDTA, 0.1% BSA and 10 mM PMSF. The washings were then centrifuged in order to remove tissue debris (10 min at 3000×g) and the supernatants were stored at −20° C. In order to determine the concentrations of total IgA in the lung and vagina washings, serial dilutions of the corresponding samples were incubated in microtiter plates with these plates having been previously coated with goat anti-mouse IgA (Sigma Chemie, Deisenhofen, Germany) as the capturing antibody (100 µl/well). Serial dilutions of purified mouse IgA (Sigma Chemie, Deisenhofen, Germany) were used for obtaining a standard curve. In order to investigate the capacity of R-MALP-2, S-MALP-2 and BPP-Cys-PEG for stimulating effective humoral immune responses, the serum titers of β-gal-specific antibodies were determined in the inoculated mice. As FIG. 3 shows, administering β-gal in the presence of BPP-Cys-PEG leads to the elicitation of antigen-specific IgG titers which rise more rapidly than those obtained using R-MALP-2.

Figure 4:
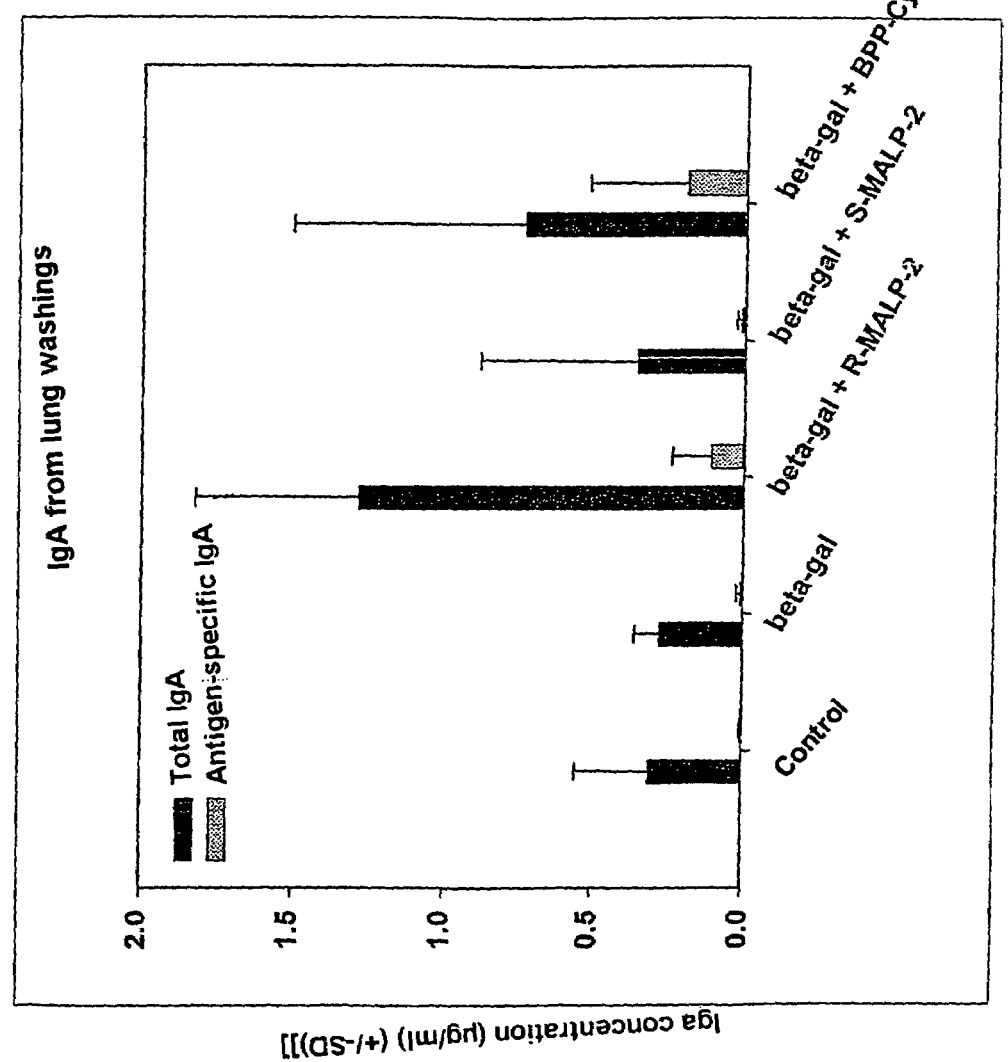
FIG. 4: Total β-gal-specific IgA in the lung washes from intranasally immunized mice. The standard deviations (SD) are depicted by vertical lines.
Figure 5:
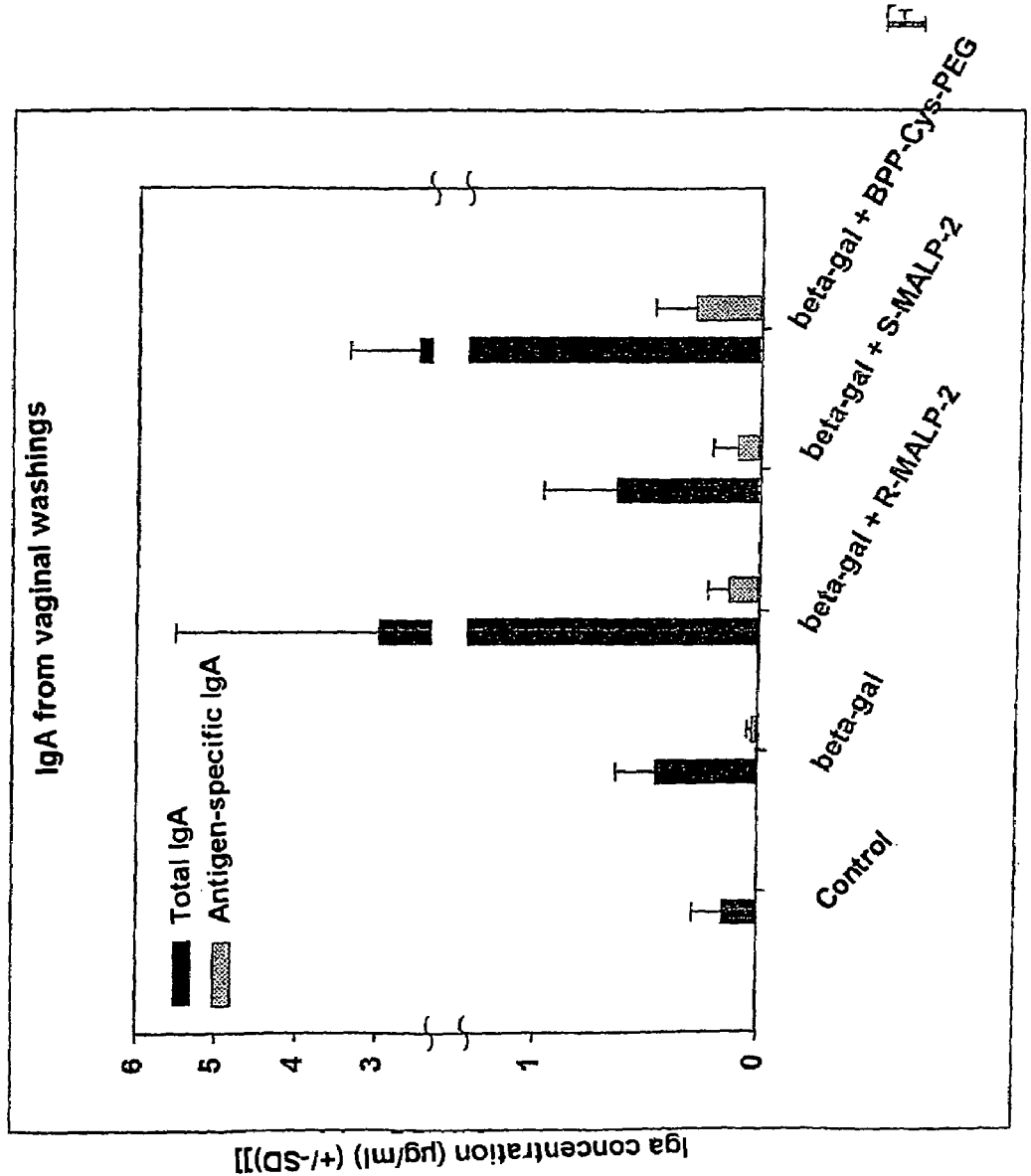
FIG. 5: Total β-gal-specific IgA in the vaginal washes from intranasally immunized mice. The standard deviations are depicted as vertical lines.

In order to determine the ability of the above derivatives to stimulate mucosal responses to antigens which were together intranasally (i.n.), the production of β-gal-specific IgA was investigated in lung and vaginal washings from immunized animals. Whereas no β-gal-specific IgA was produced in the lung washings following i.n. inoculation with pure β-gal or mixtures of β-gal and the S-MALP-2 derivative, a significant increase in antigen-specific IgA antibodies was observed in the case of the animals which were immunized with β-gal and, in addition, either R-MALP-2 or BPP-Cys-PEG (FIG. 4). The simultaneous administration of R-MALP-2, or BPP-Cys-PEG, and antigen resulted in an effective IgA production being stimulated even at distant mucosae, as was demonstrated by the presence of significant concentrations of β-gal-specific IgA in vaginal washings (FIG. 5).

4. Using BPP-Cys-PEG as a mucosal adjuvant leads to the elicitation of an effective T cell-mediated proliferation response.

Figure 6:
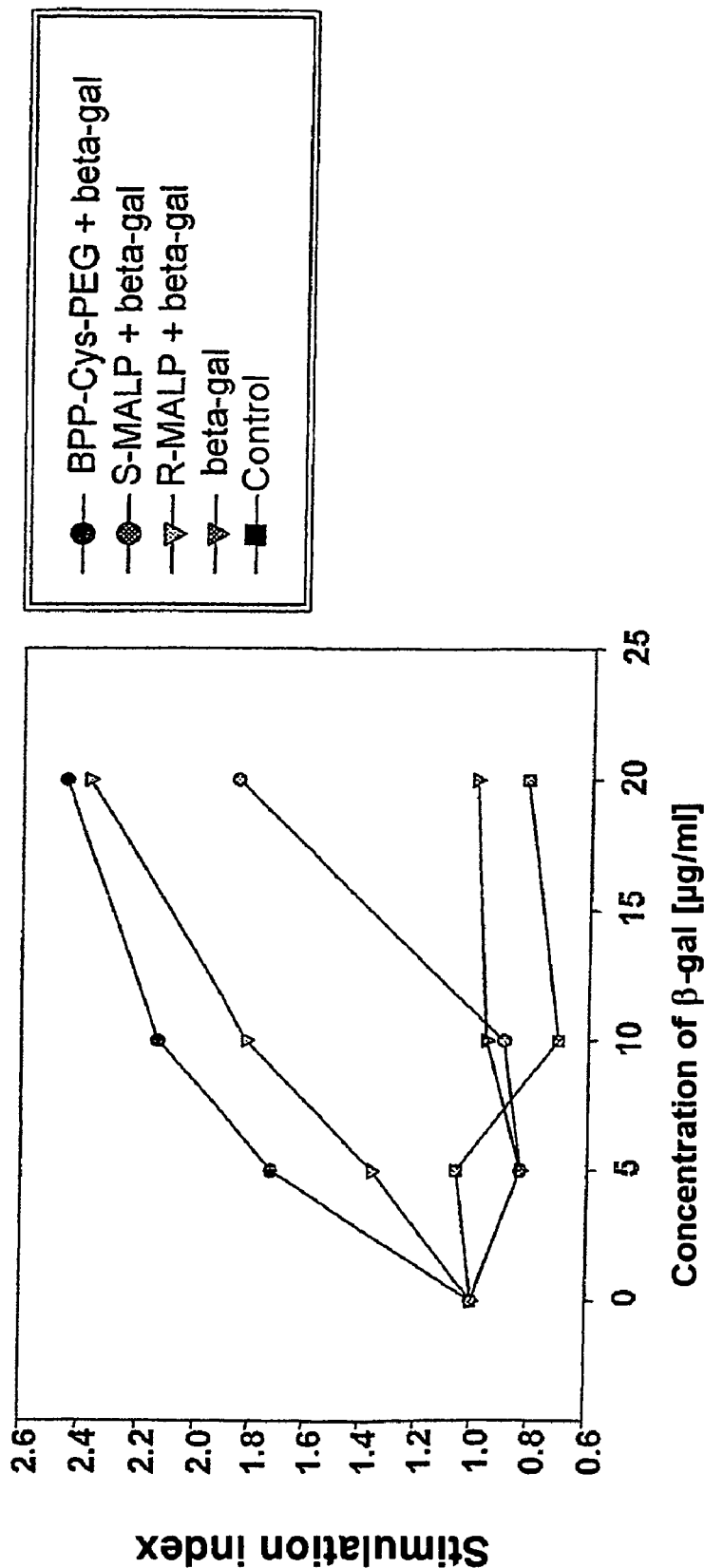
FIG. 6: β-gal-specific T cell proliferation responses of spleen cells from immunized mice. The cells were restimulated in vitro over 4 days with different concentrations of soluble β-gal. The results are depicted as ratios between the values (means of triple determinations) from stimulated and unstimulated samples (stimulation index).

Experimental Procedure:

The spleens were removed and taken together for analyzing the cell immune responses. The cells were propagated in RPMI 1640, additionally containing 10% calf serum, 100 U of penicillin/ml, 15 µg of streptomycin/ml, $5\times10^{-5}$ M 2-mercaptoethanol and 1 mM L-glutamine (GIBCO BRL, Karlsruhe, Germany), and stored at 37° C. in a moist atmosphere containing 5% $CO_2$. The cell suspensions were adjusted to $5\times10^6$ cells/ml in complete medium and sown, at the rate of 100 µl per well, in a 96-well flat-bottomed microtiter plate (Nunc); the plates were then incubated for 4 days in the presence of different concentrations of soluble β-gal. Each concentration was tested in triplicate. 1 µCi of [$^3$H]-thymidine (Amersham International, Freiburg, Germany) was added to each well for the last 8 hours of culture. These cells were then harvested on filter paper (Filtermat A; Wallac, Freiburg, Germany) using a cell harvester (Inotech, Wohlen, Switzerland) and the quantity of [$^3$H] thymidine taken up into the DNA of proliferating cells was determined using a scintillation counter (Wallac 1450, Micro-Trilux). The results were recorded as the ratios between the values (mean values, determined in triplicate) of stimulated and unstimulated samples (stimulation index). Whereas the i.n. administration of β-gal on its own did not elicit any induction of detectable cell proliferation, the simultaneous administration of R-MALP-2 or BPP-Cys-PEG together with antigen led to an effective proliferation response (FIG. 6). It is noted that the strongest T cell proliferation response was observed in the spleen cells of mice which were immunized with BPP-Cys-PEG and β-gal. Using S-MALP-2 gave a markedly weaker stimulation index and only led to restimulation when using the highest dose of β-galactosidase.

The results which were obtained clearly show that BPP-Cys-PEG is at least as effective as, or even more effective than, R-MALP-2 as a mucosal adjuvant. Effective humoral and cellular immune responses were obtained, both at the systemic level and the mucosal level, against antigens which were administered simultaneously with BPP-Cys-PEG.

The invention claimed is:

1. A bisacyloxypropylcysteine conjugate according to formula (1),

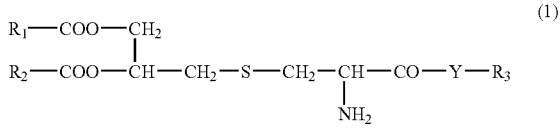

where

R₁ and R₂ can be identical or different and are $C_8$-$C_{22}$ alkyl, alkenyl or alkenyl fatty acid radicals which are bonded by way of the carboxyl group;

Y=—NH—, —O—, —S—, or —OCO—;

R₃ is a covalently bonded polyethylene glycol (polyoxyethylene)-$(CH_2—CH_2—O)_m$—$CH_2$—$CH_2$—X, where X=O(R), N(R)₂, S(R) or COO(R), and (R)=H, benzyl-, or $C_{1-6}$alkyl, where, X=N(R)₂, the (R) groups can be identical or different.

2. The bisacyloxypropylcysteine conjugate of claim 1, wherein the unsaturated positions are preferably in the cis configuration, with the $C_8$-$C_{22}$alkyl, alkenyl and alkynyl fatty acid radicals are branched or unbranched, cyclic or cycloalkyl-substituted radicals.

3. The bisacyloxypropylcysteine conjugate of claim 1, wherein a molecular weight of the covalently bonded polyethylene glycol (polyoxyethylene)-$(CH_2—CH_2—O)_m$—$CH_2$—$CH_2$—X is from 100 to 30 000 daltons.

4. The bisacyloxypropylcysteine conjugate of claim 1, wherein m is from 5 to 700.

5. The bisacyloxypropylcysteine conjugate of claim 1, wherein the bisacyloxypropylcysteine conjugate is a S-[2,3-bis(acyloxy)-(2S)-propyl]-L-cysteinylcarboxypolyethylene glycol.

6. The bisacyloxypropylcysteine conjugate of claim 1, characterized in that the compound is a S-[2,3-bis(acyloxy)-(2R)-propyl]-L-cysteinylcarboxypolyethylene glycol.

7. A pharmaceutical composition, comprising a bisacyloxypropylcysteine conjugate according to formula (1),

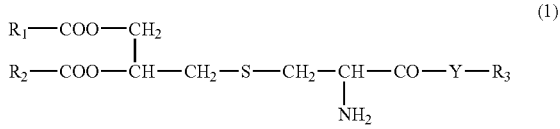

where

R₁ and R₂ can be identical or different and are $C_8$-$C_{22}$ alkyl, alkenyl or alkenyl fatty acid radicals which are bonded by way of the carboxyl group;

Y=—NH—, —O—, —S—, or —OCO—;

R₃ is a covalently bonded polyethylene glycol (polyoxyethylene)-$(CH_2—CH_2—O)_m$—$CH_2$—$CH_2$—X, where X=O(R), N(R)₂, S(R) or COO(R), and (R)=H, benzyl-, or $C_{1-6}$alkyl, where, when X=N(R)₂, the (R) groups can be identical or different.

8. The pharmaceutical composition of claim 7, further comprising a pharmaceutically tolerated excipient.

9. The pharmaceutical composition of claim 7, wherein the pharmaceutical composition is in the form of a formulation which is suitable for injection, for inhalation or for intranasal or topical administration.

10. The bisacyloxypropylcysteine conjugate of claim 4, wherein m is from 100 to 500.

11. The bisacyloxypropylcysteine conjugate of claim 5, wherein the bisacyloxypropylcysteine conjugate is S-[2,3-bis(palmitoyloxy)-(2S)-propyl]-L-cysteinylcarboxypolyethylene glycol.

12. The bisacyloxypropylcysteine conjugate of claim 6, wherein the bisacyloxypropylcysteine conjugate is S-[2,3-bis(palmitoyloxy)-(2R)-propyl]-L-cysteinylcarboxypolyethylene glycol.

13. A method of stimulating an immune response to an antigen in an animal or human, comprising the step of
simultaneously administering to the animal or human the antigen; and
a bisacyloxypropylcysteine conjugate according to formula (1),

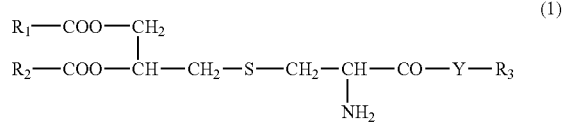

where

R₁ and R₂ can be identical or different and are $C_8$-$C_{22}$ alkyl, alkenyl or alkynyl fatty acid radicals which are bonded by way of the carboxyl group;

Y=—NH—, —O—, —S—, or —OCO—;

R₃ is a covalently bonded polyethylene glycol (polyoxyethylene)-$(CH_2—CH_2—O)_m$—$CH_2$—$CH_2$—X, where X=O(R), N(R)₂, S(R) or COO(R), and (R)=H, benzyl-, or $C_{1-6}$alkyl, where, when X=N(R)₂, the (R) groups can be identical or different.

14. A bisacyloxypropylcysteine conjugate according to formula (1),

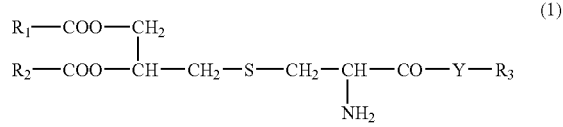

where

R₁ and R₂ can be identical or different and are $C_8$-$C_{22}$ alkyl, alkenyl or alkynyl fatty acid radicals which are bonded by way of the carboxyl group;

Y=—NH—, —O—, —S—, or —OCO—;

R₃ is a covalently bonded polyethylene glycol (polyoxyethylene)-$(CH_2—CH_2—O)_m$—$CH_2$—$CH_2$—X, where X=O(R), N(R)₂, S(R) or COO(R), and (R)=H, benzyl-, or $C_{1-6}$alkyl, where, when X=N(R)₂, the (R) groups can be identical or different, and wherein said bisacyloxypropylcysteine conjugate is a S-[2,3-bis(acyloxy)-(2S)-propyl]-L-cysteinylcarboxypolyethylene glycol.

15. A bisacyloxypropylcysteine conjugate according to formula (1),

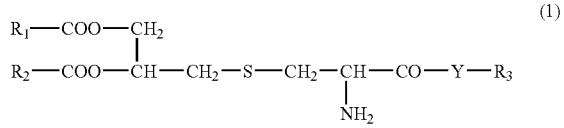

where
- $R_1$ and $R_2$ can be identical or different and are $C_8$-$C_{22}$ alkyl, alkenyl or alkynyl fatty acid radicals which are bonded by way of the carboxyl group;
- Y=—NH—, —O—, —S—, or —OCO—;
- $R_3$ is a covalently bonded polyethylene glycol (polyoxyethylene)-$(CH_2—CH_2—O)_m—CH_2—CH_2—X$, where X=O(R), N(R)$_2$, S(R) or COO(R), and
- (R)=H, benzyl-, or $C_{1-6}$alkyl, where, when X=N(R)$_2$, the R groups can be identical or different, and wherein said bisacyloxypropylcysteine conjugate is a S-[2,3-bis(acyloxy)-(2R)-propyl]-L-cysteinylcarboxypolyethylene glycol.

* * * * *